United States Patent [19]
Sikkenga et al.

[11] Patent Number: 5,034,561
[45] Date of Patent: * Jul. 23, 1991

[54] CATALYTIC ALKENYLBENZENE CYCLIZATION

[75] Inventors: David L. Sikkenga, Wheaton, Ill.; Gregory S. Williams, Tampa, Fla.; Ian C. Zaenger, Wheaton, Ill.

[73] Assignee: Amoco Corporation, Chicago, Ill.

[*] Notice: The portion of the term of this patent subsequent to Jul. 9, 2008 has been disclaimed.

[21] Appl. No.: 539,087

[22] Filed: Jun. 15, 1990

[51] Int. Cl.$^5$ ................................................ C07C 5/00
[52] U.S. Cl. ...................................... 585/411; 585/410
[58] Field of Search ............... 585/411, 400, 410, 320, 585/430

[56] References Cited

U.S. PATENT DOCUMENTS 3,997,616 12/1976 Tokashiki et al. .................. 585/411

FOREIGN PATENT DOCUMENTS 5022551 10/1970 Japan .................................. 585/411
5058050 9/1973 Japan .................................. 585/411

Primary Examiner—Curtis R. Davis
Attorney, Agent, or Firm—James R. Henes; William H. Magidson; Ralph C. Medhurst

[57] ABSTRACT

A method is provided for cyclizing an alkenylbenzene to a dialkyltetrahydronaphthalene (dialkyltetralin) in the presence of a solid cyclization catalyst constituted by a relatively low acidity, ultrastable, hydrogen form of crystalline aluminosilicate zeolite Y having a sodium oxide-to-alumina bulk molar ratio in the range of about 0.001 to about less than 1, a unit cell size no greater than about 24.3 Angstroms, and a sodium content of no more than about 0.4 percent by weight, calculated as elemental sodium and based on the weight of the zeolite. This catalyst provides more activity, more stability, higher product purity, and higher product yields than known prior art zeolite cyclization catalysts notwithstanding its relatively lower acidity. A preferred alkenylbenzene is 5-(o-tolyl)-pent-2-ene which is converted in relatively high yields and relatively high selectivities to 1,5 dimethyltetrahydronaphthalene.

28 Claims, 1 Drawing Sheet

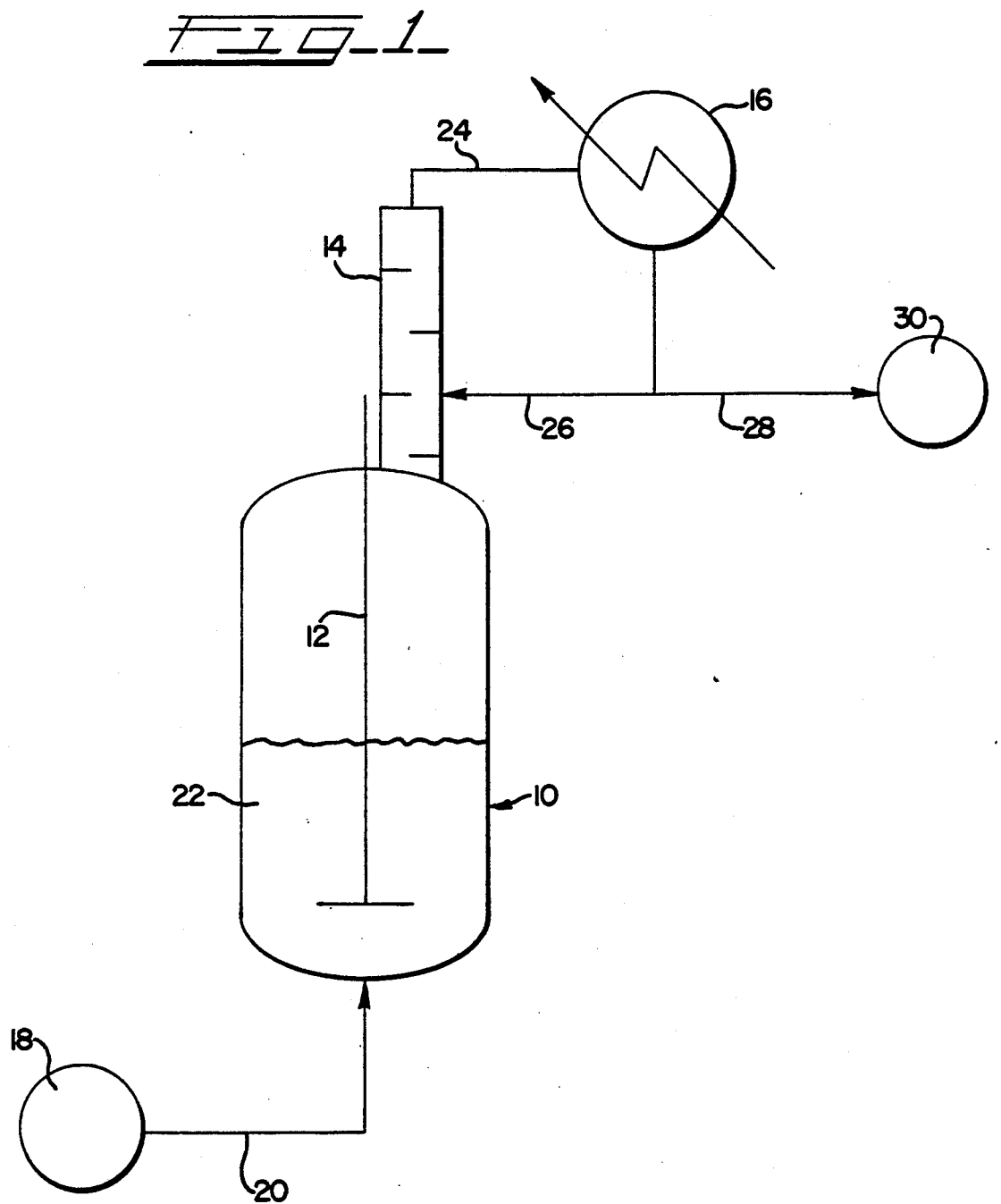
FIG_1

CATALYTIC ALKENYLBENZENE CYCLIZATION

RELATED APPLICATION

This application is related in U.S. Patent application No. 539,007 of D. L. Sikkenga, I. C. Zaenger and G. S. Williams, filed concurrently herewith.

FIELD OF THE INVENTION

This invention relates to a catalytic process for cyclizing alkenylbenzenes to the corresponding dialkyltetrahydronaphthalenes.

BACKGROUND OF THE INVENTION

Dialkylnaphthalenes, such as 2,6-dimethylnaphthalenes, are desirable starting materials for oxidation to the corresponding naphthalene dicarboxylic acids. Such acids are monomers that are useful for the preparation of a variety of polymers. For example 2,6-naphthalene dicarboxylic acid when polymerized with ethylene glycol produces poly(ethylene 2,6-naphthalate) which can have better heat resistance and mechanical properties than polyethylene terephthalate, and which can be used to make films, fibers, and the like.

In refinery streams derived from petroleum or coal, dimethylnaphthalenes are present as isomeric mixtures which are difficult and costly to separate. Hence, techniques for producing specific dimethylnaphthalenes alone or in admixture with one or two other specific isomers are highly desirable. One promising process is to catalytically cyclize one or more alkenylbenzenes into the corresponding dialkyltetralins, i.e., dialkyltetrahydronaphthalenes, which are then dehydrogenated to the corresponding dialkylnaphthalenes. A mixture of such dialkylnaphthalenes, such as a mixture of triad of 1,6-, 1,5-, and/or 2,6-dimethylnaphthalenes, can then be isomerized to a single such product, such as 2,6-dimethylnaphthalene. Such a cyclization, dehydrogenation, and isomerization process sequence is described, for example, in commonly assigned Sikkenga et al., copending U.S. Patent application Ser. No. 316,308 filed Feb. 27, 1989.

The catalyst heretofore employed for the cyclization of the alkenylbenzenes in such process usually is an acidic, ultrastable, Y-type zeolite catalyst in hydrogen form, having a unit cell size of about 24.2 to about 24.7 Angstroms, and $SiO_2$ to $Al_2O_3$ molar ratio of about 4:1 to about 6:1, and a sodium content of from about 0.05 to about 3.5 weight percent, calculated as elemental sodium and based on the weight of the zeolite. It has now been found, however, that as less acidic catalyst of the same general type, i.e., one having a substantially higher $SiO_2$ to $Al_2O_3$ molar ratio and a low $Na_2O$ content provides an unexpectedly improved cyclization of alkenylbenzenes in higher yields and with improved selectivity.

SUMMARY OF THE INVENTION

The present invention provides an improved method for catalytically cyclizing alkenylbenzenes to the corresponding dimethyltetrahydronaphthalenes in relatively higher yields.

This method employs a relatively low acidity, ultrastable, crystalline zeolite Y catalyst that is substantially free of absorbed water, that exhibits Bronsted acidity, but has:

a unit cell size no greater than about 24.3 Angstroms, and a sodium content of no more than 0.4 weight percent calculated as elemental sodium and based on the weight of the crystalline zeolite, or in terms of the $Na_2O$ to $Al_2O_3$ bulk molar ratio, in the range of about 0.001:1 to less than about 1:1.

The $SiO_2/Al_2O_3$ bulk molar ratio for such a catalyst is at least about 12, and preferably is at least about 30.

The present method is practiced by contacting a liquid alkenylbenzene feed stream containing no more than about 0.1 weight percent water with such a catalyst while maintaining a temperature in the range of about 120° C. to about 350° C. and a pressure sufficient to maintain the reactants substantially in liquid state during cyclization.

Various other features, advantages, aims, purposes, embodiments, and the like of this invention will be apparent to those skilled in the art from the present specification and appended claims.

BRIEF DESCRIPTION OF THE DRAWING

In the drawing, FIG. 1 is a schematic flow diagram illustrating a continuous cyclization process embodying the present invention.

DETAILED DESCRIPTION OF THE PREFERRED EMBODIMENTS

The present invention provides a method for the cyclization of an alkenylbenzene having the formula

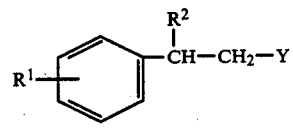

wherein $R^1$ can be a member of the group consisting of hydrogen, methyl, and ethyl, $R^2$ can be a member of the group consisting of hydrogen and methyl, and Y is an alkenyl of the group consisting of $-CH=CH-CH_3$ and $-CH_2-CH=CH_2$. This method contemplates contacting such an alkenylbenzene, in liquid form and having a water content of no more than about 0.1 weight percent, with a solid, particulate cyclization catalyst which is relatively low acidity, ultrastable hydrogen form of crystalline aluminosilicate zeolite Y, i.e., a molecular sieve of having a cubic, faujasite crystalline structure. The contemplated zeolite Y catalyst has a silica-to-alumina bulk molar ratio of at least about 12, a unit cell size no greater than 24.3 Angstroms, a sodium content of no more than about 0.4 weight percent, preferably no more than about 0.25 weight percent, calculated as elemental sodium and based on the weight of the zeolite or in terms of the sodium oxide-to-alumina bulk molar ratio in the range of from about 0.001:1 to about 1:1.

Cyclization of the alkenylbenzene is carried out in the liquid phase, at a temperature in the range of about 120° C. to about 350° C., and preferably under reflux conditions. Reaction pressure is selected so as to maintain the reactant and the reaction products in the liquid phase while cyclization proceeds. The catalyst contact time with the alkenylbenzene can vary, but is sufficient to produce a liquid product that is enriched in a dialkyltetrahydronaphthalene derived from the alkenylbenzene.

The term "relatively low acidity" as used herein in reference to a zeolite useful for the practice of this invention has reference to the relatively few Bronsted acid sites in the crystalline zeolite framework that provide sufficient acidity to catalyze the desired cyclization but without the production of undesirably large amounts of by-products.

Substances that owe their acidity to the presence of protons are termed Bronsted acids. In the case of crystalline aluminosilicates or zeolites, a Bronsted acid site occurs in the crystalline zeolite framework where an aluminum atom surrounded by four oxygen atoms is present. Inasmuch as some of such Bronsted acid sites are neutralized by alkali metal presence in the crystalline framework, the Bronsted acidity of a particular zeolite can be delineated by specifying the bulk molar ratios of $SiO_2/Al_2O_3$ and $N_2O/Al_2O_3$ as set forth hereinabove. In terms of the number of framework Bronsted acid sites per unit cell of the crystalline zeolite catalyst, for the purposes of the present method the catalyst has an average of no more than about 10 framework Bronsted acid sites, preferably no more than about 4 such sites, per unit cell.

The term "ultrastable" as used herein in reference to a zeolite has reference to a zeolite which has been thermally stabilized by dealumination to produce a synthetic zeolite having much improved resistance to degradation under acid and hydrothermal conditions.

The term "zeolite Y" as used herein in reference to the contemplated crystalline aluminosilicate molecular sieve has reference to a zeolite which has the characteristic framework structure of the faujasite mineral class.

The term "bulk molar ratio" as used herein denotes the molar ratio of the designated moieties regardless of whether present in the crystalline framework of the molecular sieve or not.

The ultrastable, zeolite Y employed as a catalyst in the process of the present invention is a low alumina ($Al_3O_3$)-containing, low sodium (or low sodium oxide)-containing Y-type molecular sieve material that is in hydrogen form and has relatively low acidity. The catalyst pore windows or apertures are defined by twelve tetrahedral atoms. The catalyst framework alumina concentration for such a zeolite is also indicated in part by the unit cell size which, as measured by x-ray diffraction, is no more than about 24.3 Angstroms. The $SiO_2$ to $Al_2O_3$ bulk molar ratio is above about 12, and preferably is at least about 30. Expressing the sodium content in terms of sodium oxide, the $Na_2O$ to $Al_2O_3$ bulk molar ratio is in the range of about 0.001 to less than about 1, preferably in the range of about 0.01 to about 0.05.

It is also important for the zeolite catalyst used in the process of this invention to have a relatively low sodium content, as reported in terms of sodium oxide, of less than about 0.4 weight percent (on zeolite weight basis), and preferably less than about 0.25 weight percent.

A presently preferred ultrastable, zeolite Y having such a combination of low acidity, cell size, $Na_2O$-to-$Al_2O_3$ and $SiO_2$-to-$Al_2O_3$ molar ratios, and $Na_2O$ content is available commercially under the trade designation "Conteka CBV 760" from the Conteka Company, Leiden, The Netherlands. This particular catalyst is in powder form and has a $Na_2O/Al_2O_3$ bulk molar ratio of about 0.05, a $SiO_2/Al_2O_3$ bulk molar ratio of 50, and a sodium content of 0.075 weight percent, calculated as elemental sodium and based on the weight of the zeolite. This catalyst has a unit cell size of 24.2 Angstroms and a surface area of 720 $m^2/g$. Another suitable such zeolite Y catalyst is available commercially from P Q Corporation, Valley Forge, Penna., under the trade designation "Valfor CP 301-26". This particular catalyst is in powder form and has a unit cell size of 24.25 Angstroms, an $SiO_2/Al_2O_3$ bulk molar ratio of about 80, a sodium content of about 0.023 weight percent, calculated as elemental sodium and based on the weight of the zeolite, and a surface area of about 775 $m^2/g$. The $Na_2O/Al_2O_3$ bulk molar ratio for this particular catalyst is about 0.02.

The present zeolite catalyst, as used in the present cyclization process, can be either in a powdered form or in a granular form. A powdered catalyst is conveniently mechanically dispersed by mixing action in the liquid phase reactant employed. When in a granular form, the granule size can vary widely, such as from about 1/32" to about 1 inch in average maximum diameter, the exact size in any given instance being influenced by the choice of particular fixed-bed reactor wherein the granular form is to be employed and through which the liquid phase reactant is circulated. As used herein, the term "granular form" is generic to porous structures having the various possible physical shapes, and made by the various possible preparation methods, including compacting, extruding, and the like, and such term is inclusive of both supported and unsupported zeolite catalyst forms.

When supported, the zeolite Y catalyst can be supported on a porous refractory inorganic oxide that is inert under the cyclization conditions employed. Illustrative such oxides include silica, alumina, silica-alumina, magnesia, bentonite or other such clay, and the like. Presently preferred such oxides are silica, alumina, and silica-alumina. In such a supported catalyst, the zeolite can comprise at least about 10 weight percent of the total supported catalyst up to about 90 weight percent thereof with a present preference being to employ a quantity of zeolite that is in the range of about 20 to about 80 weight percent thereof.

Preferred alkenylbenzenes for use in the practice of the method of this invention are 5-(monomethylphenyl)-pent-1-ene, 5-(monomethylphenyl)-pent-2-ene, 5-(phenyl)-hex-1-ene, 5-(phenyl)-hex-2-ene, and mixtures thereof. Examples include 5-(o- m-, or p- tolyl)-pent-1- or 2-ene, and 5-phenyl-hex-1-or -2-ene.

To minimize production of isomeric product mixtures, it is presently preferred to employ as the reactant feedstock one which is comprised of at least about 90 weight percent on a total feedstock weight basis of a specific alkenylbenzene, exclusive of any solvent that may be present, and more preferably which is comprises of at least about 98 weight percent of such an alkenylbenzene. Most preferably, such a feed comprises a substantially pure alkenylbenzene compound. By the term "substantially pure" as used herein reference is had to a composition which consists of at least about 99 weight percent on a 100 weight percent basis of a single compound.

A presently most preferred alkenylbenzene for practicing the method of this invention is 5-(o-tolyl)pent-2-ene (OTP).

The feed used in the practice of this invention should be substantially free of moisture and of other non-hydrocarbon components. The presence of water temporarily deactivates the zeolite catalyst when operating at temperatures of less than about 230° C. Non-hydrocarbon components can be, or can contain or form, agents which poison the catalyst. Examples of such components or agents include amines, metal cations, and the like.

To cyclize an alkenylbenzene in accord with this invention, one contacts such compound with the ultrastable zeolite Y catalyst as herein described while maintaining the resulting admixture at a temperature in the range of about 120° C. to about 350° C. and at a pressure sufficient to maintain the hydrocarbon reactants substantially in a liquid phase for a time period sufficient to enrich the product with the corresponding dialkyltetrahydronaphthalene.

Preferred cyclization temperatures are in the range of about 160 to about 250° C. Since the cyclization occurs in the liquid phase, pressure is not critical to the reaction and is dictated primarily by the reaction temperature. During a cyclization reaction, reaction pressure is preferably adjusted to maintain the reactants substantially in a liquid phase. Suitable reaction pressures can be in the range of about 2.5 psia to about 525 psia.

In general, the quantity of the zeolite catalyst employed in a reaction zone for cyclization is that sufficient to be catalytically effective. Catalyst concentration can be varied to optimize the reaction rate. Concentrations of the zeolite catalyst in the range of about 0.1 to about 10 weight percent based on total reactor charge are presently preferred, with a catalyst concentration in the range of about 0.3 to about 2 weight percent (same basis) being more preferred; however, larger and smaller amounts of the catalyst can be employed, if desired.

The cyclization of the alkenylbenzenes to dialkyltetrahydronaphthalenes can be carried out batch-wise, continuously, or semicontinuously, as desired. During cyclization, the alkenylbenzene preferably is comingled with the corresponding, preformed dialkyltetrahydronaphthalene.

A continuous cyclization process is schematically illustrated in FIG. 1. Reactor 10 is equipped with agitator 12, reflux column 14 and overhead condenser 16. Alkenylbenzene feedstock from an appropriate source 18 is fed via line 20 to reactor 10 that is maintained at steady state reflux conditions containing a boiling liquid admixture 22 of reactants and reaction products together with the particulate zeolite catalyst suspended therein. The relatively lower boiling feedstock is introduced into the reactor below the liquid level therein while the cyclized product is withdrawn from the reactor 10 via reflux column 14 and is conveyed to overhead condenser 16 via line 24. The withdrawn product is condensed in condenser 16 and a portion thereof is returned to reactor 10 by means of reflux line 26 while the remainder is transported to product storage 30 via product line 28. The relatively high activity of the presently contemplated catalysts permits the illustrated "heavies recycle" without loss of feedstock to the reflux column. That is, the feedstock is converted to a cyclized product before the feedstock can be flashed under the temperature and pressure conditions prevailing in the reactor. Analyses of cyclized product obtained utilizing the aforesaid "heavies recycle" technique have indicated less than about 1 weight percent of feedstock material in the cyclized product.

Batch cyclization is preferably carried out until substantially all of the alkenylbenzene present is converted. Thereafter, the product dimethyltetrahydronaphthalene can be readily separated from the reaction mass by flash distillation.

To carry out a batch type process, a stirred tank reactor where the zeolite catalyst is present in powdered form can be utilized. At startup, an initiator batch is preferably produced in such a reactor. Such a batch comprises the zeolite catalyst and a non-reactive hydrocarbon which is substantially in a liquid phase under the contacting conditions. While the choice of such a non-reactive hydrocarbon can vary widely and is not critical, it is presently preferred to employ as such hydrocarbon a dimethyltetrahydronaphthalene, particularly the specific dimethyltetrahydronaphthalene sought to be produced in the batch process.

The reactant feed, which is substantially free of moisture and other non-hydrocarbon components as above indicated, is added to a batch reactor that preferably already contains such an initiator batch therein. The presently most preferred feed is substantially pure OTP.

Feed addition is carried out at a rate which allows heat removal and control of temperature in the reactor so that the reactant and reaction product temperature in the liquid phase is maintained at a level which is within the above indicated temperature range.

After a chosen quantity of the feed has been so added and has been converted to the corresponding dialkyltetrahydronaphthalene, the latter is removed from the reactor by flash distillation. Left behind in the tank is a "heel" composition that includes the zeolite catalyst, optionally some residual dimethyltetrahydronaphthalene product, and hydrocarbon by-products having molecular weights higher than about 160, i.e., above the molecular weight of a dialkyltetraydronaphthalene. Such hydrocarbon by-products typically comprise dimers of the alkenylbenzene and the produced dialkyltetrahydronaphthalene.

During the post-reaction flash distillation, at least about 60 weight percent of the dimethyltetrahydronaphthalene, based on the total product dimethyltetrahydronaphthalene estimated to be present in the reactor at the termination of the batch reaction, is removed.

Thereafter, an additional chosen quantity of the feed is added to the heel composition present in the tank. As before, the feed addition rate is preferably such as to allow heat removal during cyclization and temperature control. After the desired conversion of the feed is achieved, the flash distillation step is repeated to remove additional product from the reactor.

Such a batch step sequence can be repeated for a number of cycles as long as catalyst activity can be maintained. With repeated cycles, however, a build-up of the above indicated hydrocarbon by-products to an equilibrium level may occur in reactor.

When the level or quantity of such by-products has reached some chosen point, a cracking procedure can be carried out concurrently or sequentially to decompose relatively larger molecules into smaller, lower boiling molecules, some of which are alkenylbenzenes. At the same time, such alkenylbenzenes present react and cyclize to dialkyltetrahydronaphthalenes. In such a procedure, if performed sequentially, the heel composition that is produced as a result of a preceding batch cycle or cycles as above characterized is heated to a temperature in the range of about 180° C. to about 350° C. and at a pressure sufficient to maintain such heel composition substantially in a liquid phase, so as to convert the indicated dimers in such heel composition into additional dialkyltetrahydronaphthalene which is then removed by flash distillation from the reactor. Thus, the same zeolite Y catalyst serves two functions.

Yields of dimethyltetrahydronaphthalene are thereby maximized.

In one presently particularly preferred mode of practicing the process of this invention, 1,5-dimethyltetrahydronaphthalene is made by cyclizing 5-(o-tolyl)-pent-2-ene (OTP). To that end, an initiator batch comprised of the powdered catalyst and 1,5-dimethyltetrahydronaphthalene is first formed in a stirred tank reactor by 100% conversion of an OTP charge using temperature and pressure conditions as above described. The amount of catalyst used is such that, after the addition of the OTP in the next step (described below), the concentration of the zeolite catalyst is in the aforesaid preferred range.

Next, the substantially pure OTP that is substantially free of moisture and also of non- hydrocarbon components is added to the reactor maintained at a temperature in the range of about 160° C. to about 250° C., and at a pressure sufficient to maintain the reactants in a liquid phase. The OTP addition is carried out at a rate which allows heat removal and control of temperature in the reactor at a chosen reflux level which is within the above indicated temperature range.

The reactor is maintained at such a chosen reflux level while the pressure is gradually reduced to a level which is sufficient to maintain a chosen reflux level until substantially all of the OTP has been converted.

Finally, about 75 to about 80 weight percent of the thus formed 1,5-dimethyltetrahydronaphthalene is flash distilled from the reactor.

The foregoing conversion steps are then sequentially repeated at least once. As the Examples hereinbelow indicate, this sequence can be repeated at least seven times without noticeable catalyst deactivation; thus, no increase in reaction temperature or in reaction time is needed to complete the OTP conversion in subsequent batches. The amount of useful products produced for seven such batches was 4.1% higher than the amount of useful product produced in a comparable procedure carried out using a more acidic zeolite Y catalyst. Such increase also represents a 49% by weight reduction in final product impurities. In addition, for such seven batches, the cumulative yield of useful components was increased from 85% in such comparable procedure to 90% when using the presently contemplated catalyst. The amount of undesired dimethyltetrahydronaphthalene isomers concurrently decreased from 1.2 percent by weight to an average of about 0.9 percent by weight.

The catalyst employed in the present invention is more active and more stable, and gives higher product purity with higher yield, than is possible with the more acidic catalysts heretofore employed for the cyclization of alkenylbenzenes.

Moreover, the thermal stability of the present catalyst permits multiple successive batch runs to be carried out, each batch using similar conditions without adding additional catalyst. In addition, when the heavy by-products accumulate, they can be selectively converted to useful products by a cracking procedure using the same catalyst and the same reactor. The use of this catalyst in a fixed-bed reactor provides equally positive results.

In this manner the alkenylbenzene feed is rapidly converted to a useful product, thereby avoiding a dangerously high concentration of feed, such as, for example, OTP, in the reactor. The capacity to flash distill and separate desired product from catalyst and heavy by-products, thereby leaving the reactor ready for use in a next batch provides a safe, cost effective, and advantageous process that is efficient to operate.

The zeolite catalyst employed herein exhibits an unusually low isomerization activity. Thus, a reaction product can be maintained for extended periods of time in the presence of the catalyst with substantially no product degradation into isomers. This feature is illustrated in Example 18, below.

A presently preferred class of cyclized products includes dimethyltetrahydronaphthalene isomers which can be readily dehydrogenated. Suitable conversion procedures are known to the prior art.

The present invention is illustrated by the following examples.

In these Examples, the term "useful product" refers to all useful components in a cyclized product, including all dimethyltetrahydronaphthalene (termed DMT) isomers and all dimethylnaphthalene (termed DMN) isomers which can be converted by dehydrogenation and isomerization into the desired 2,6-dimethylnaphthalene. In these examples, such "DMT isomers" are the 1,5-, 1,6- 2,5- and 2,6-DMT isomers.

EXAMPLES 1-16

COMPARISON OF HIGH ALUMINA CONTENT WITH LOW ALUMINA CONTENT ACIDIC, ULTRASTABLE Y-TYPE ZEOLITE CATALYSTS

To compare a relatively high alumina content, acidic, ultrastable, Y-type zeolite catalyst ("Catalyst A") with a relatively low alumina content ultrastable, Y-type zeolite catalyst ("Catalyst B"), the following zeolite catalyst materials were used:

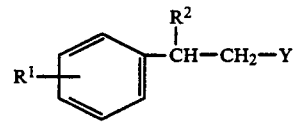

Catalyst A was a catalyst commercially available from the Union Carbide Company, Danbury, Conn., under the trade designation "LZ-Y72". Catalyst B was a catalyst commercially available from the Conteka Company under the trade designation "Conteka CBV 760". For each catalyst, the following procedure was used:

A 1000 ml flask fitted with a magnetic stirrer, reflux condenser, and distillation/collection head was charged with 1.8 g of powdered catalyst and 150 g of 98% by weight (based on total hydrocarbon feedstock) of 5-(o-totyl)pent-2-ene (OTP). The flask was brought to a pressure of 6 psia and 180°-190° C. at which point the reactor contents were at reflux. Thereafter, the pressure was gradually decreased as the OTP was converted while the temperature and reflux were maintained. This conversion took about 2-4 hours and the product comprised about 88 weight percent (100 weight percent product basis) dimethyltetrahydronaphthalene, the remainder being constituted by heavy and light by-products. The converted OTP in the first 150 g batch served as a "heel" composition for the second and subsequent successive batches. The results are compiled in Tables 2 and 3 below.

In Table 2 results with Catalyst A are reported, while in Table 3 results with Catalyst B are reported. The amount of OTP fed and the amount of product produced is shown in each Table along with batch operating conditions.

For the first full batch (#1 in each of Tables 2 and 3), 5.4 g of additional catalyst was introduced into the flask. After reflux was established in the reactor at 180°–190° C., for each batch an additional 440 g of OTP was added over a time period of 2 hours. This procedure is preferred in a larger scale commercial operation because heat generation can be controlled by the rate of OTP addition in this manner. Following the OTP addition, the reaction admixture was maintained at reflux at the above-stated temperature until all of the added OTP was converted as determined by gas chromatography. Typically, about 2–5 hours was required after OTP addition to achieve complete conversion. About 75% of the product produced in each batch was then flash distilled from the reactor, leaving about 25% of the product as the heel for the next batch. The heavy by-products and all the catalyst remained in the heel. For each of Batches 2–7, no additional catalyst was added. The amount of OTP added for each batch was about the same as the amount of cyclized product removed from the previous batch.

7 full batches, the cumulative amount of useful product obtained was 0.85 grams/gram of OTP (84%).

In the case of Catalyst B (see Table 3), the relatively higher activity thereof allowed operation at 180° C. with shorter reaction times than was possible with Catalyst A. In the 7 batches, no catalyst deactivation was observed, so no increase in temperature or reaction time was necessary to complete the OTP conversion. The weight percent of useful products for the 7 batches was in the range of about 94.8% to about 96.2%, and averaged 95.7%. This is an average increase of 4.1% over the yield obtained with Catalyst A in Examples 1–8. This represents a 49% reduction in impurities for the final useful product. In addition, the cumulative yield of components in the useful product increased from 85% for such comparison Catalyst A to 90% for the present improved Catalyst B. The amount of undesired DMT isomers decreased from 1.2% using the comparison Catalyst A to an average of 0.9% for Catalyst B. Thus, Catalyst B was more active under the present process conditions, more stable, and gave higher product purity as well as higher yield than Catalyst A.

TABLE 2

CYCLIZATION OF OTP USING CATALYST A

| Example | Batch | Temp, C. | Reaction Time (Hr) | Amt. Feed Grams | Amt. Prod Grams | Wt. % Useful In Product | Wt. % DMT Isom | Cumulative G Useful/G OTP |
|---|---|---|---|---|---|---|---|---|
| 1 | HEEL | 190 | 4.5 | 150.0 | 2.8 | 88.3 | 1.03 | 0.00 |
| 2 | 1 | 190 | 4.0 | 440.0 | 437.7 | 92.3 | 1.12 | 0.69 |
| 3 | 2 | 200 | 7.0 | 440.0 | 454.2 | 92.8 | 1.07 | 0.80 |
| 4 | 3 | 216 | 8.0 | 440.0 | 387.9 | 92.4 | 1.17 | 0.81 |
| 5 | 4 | 237 | 2.8 | 403.0 | 415.6 | 90.6 | 1.34 | 0.83 |
| 6 | 5 | 238 | 2.8 | 417.0 | 411.4 | 90.9 | 1.27 | 0.84 |
| 7 | 6 | 238 | 2.8 | 420.6 | 405.9 | 91.2 | 1.22 | 0.85 |
| 8 | 7 | 238 | 2.8 | 406.6 | 391.4 | 91.2 | 1.22 | 0.85 |
| TOTALS | | | | 3117.2 | 2906.9 | | | |
| Average Batches 1–7 | | 222 | 4.3 | | | 91.6 | 1.2 | |

TABLE 3

CYCLIZATION OF OTP USING CATALYST B

| Example | Batch | Temp, C. | Reaction Time (Hr) | Amt. Feed Grams | Amt. Prod Grams | Wt. % Useful In Product | Wt. % DMT Isom | Cumulative G Useful/G OTP |
|---|---|---|---|---|---|---|---|---|
| 9 | HEEL | 180 | 3 | 150 | 1.8 | 88.8 | 0.89 | 0.01 |
| 10 | 1 | 180 | <2.0 | 448 | 431.8 | 94.8 | 0.91 | 0.69 |
| 11 | 2 | 180 | <2.0 | 450 | 442.5 | 96.2 | 0.86 | 0.80 |
| 12 | 3 | 180 | <2.0 | 439 | 412.1 | 96.0 | 0.88 | 0.83 |
| 13 | 4 | 180 | <2.0 | 420 | 421.2 | 95.8 | 0.90 | 0.86 |
| 14 | 5 | 180 | <2.0 | 450 | 455.2 | 96.1 | 0.89 | 0.88 |
| 15 | 6 | 180 | <2.0 | 441 | 443.0 | 95.6 | 0.95 | 0.89 |
| 16 | 7 | 180 | <2.0 | 451 | 444.7 | 95.6 | 0.89 | 0.90 |
| TOTALS | | | | 3249 | 3052.3 | 95.7 | 0.90 | |
| Average | | 180 | <2.0 | | | | | |

In the case of Catalyst A (see Table 2), the catalyst gradually deactivated with successive batch runs, requiring batch temperature increases or reaction time increases to compensate for such catalyst deactivation. The weight percent of useful product in each batch was in the range of about 90.6 to about 92.8 weight percent, based on total batch product. The average weight percent of useful product produced was 91.6% Batches 1 through 7. The amount of undesired DMT isomers was in the range of about 1.07% to about 1.34%, and averaged 1.2%. The cumulative amount of useful product removed from the system is listed in the far right column of the Table 2. The yield in early runs was low since a heel of the product remains in the system. After

EXAMPLE 17

Cracking of Heavy By-Products with Low Aluminum Ultrastable Y-Catalyst

Following the seven batch runs described in Examples 9–16, a residue remained in the reactor vessel. This residue consisted mainly of high molecular weight dimers formed by the reaction of OTP with DMT. These dimers were cracked back to DMT by extended heating solely in the presence of the catalyst at relatively low pressure. The DMT, once thus formed, was flash distilled out of the reactor.

The residue contained 7.2 g of the Catalyst B which had previously been used for the seven cycles of DMT production from OTP. The conversion was carried out at 220° C. and 127 Torr (2.5 psia) for 2 hours. The heavy by-product dimers comprised 71% (138.6 g) of the heel composition. The balance of the heel composition was DMT and DMN isomers.

A distilled product (128 g) containing 92.1% (117.9 g) useful components was obtained. The residue in the reactor contained 26.7 wt % useful components and 66.5% heavy dimers. Thus, 67.8 wt % of the heavies in the residue were converted to useful product with a selectively of 88 wt %. This additional amount of useful product represents a 4 wt.-% increase in yield to 0.94 lbs of useful product/lb of 98 wt.-% pure OTP.

This procedure is, in practice, an extension of the normal flash distillation procedure and only requires additional reaction time.

The results of this cracking procedure are shown in Table 4, below.

TABLE 4

CONVERSION OF HEAVY BY-PRODUCTS USING CATALYST B

|  | Total | Useful Product | Undesired DMT Isomers | Heavies | Other |
|---|---|---|---|---|---|
| Feedstock |  |  |  |  |  |
| Grams | 195 | 53.2 | 0.5 | 138.6 | 2.7 |
| Wt % | 100 | 27.3 | 0.3 | 71.1 | 1.4 |
| Product Distilled |  |  |  |  |  |
| Grams | 128 | 117.9 | 2.2 | 0.2 | 7.8 |
| Wt % | 65.6 | 92.1 | 1.7 | 0.1 | 6.1 |
| Product-Residue |  |  |  |  |  |
| Grams | 67 | 17.9 | 0.4 | 44.6 | 4.2 |
| Wt % | 34.4 | 26.7 | 0.5 | 66.5 | 6.3 |
| Total-Product Wt | 195 | 135.8 | 2.5 | 44.7 | 12.0 |

EXAMPLE 18

Low Isomerization Activity of Presently Contemplated Low Alumina, Ultrastable Y-Type Catalyst a batch conversion of OTP was conducted with a fresh sample of the Catalyst B and using a catalyst loading as employed in the procedure of Examples 9-16. Specifically, the present process procedure employed 10.2 g of previously prepared dimethyltetrahydronaphthalene, 94.4 g of OTP, and 0.32 g of Catalyst B. The temperature was 190° C., and the pressure was 203 Torr (3.9 psia). A complete conversion of OTP was observed after 2 hours with 94.9% selectivity to useful product. After 18 hours, the conversion of OTP was still 100% with selectivity to useful product being 94.1%.

Following complete conversion of the OTP in two hours, the reactor was allowed to reflux at 190° C. for an additional 16 hours to simulate a very show flashing step. The results are shown in Table 5 below. These results indicate that over a period of 16 hours the loss of useful products was only 0.6%. No increase in the amount of undesired DMT isomers was observed.

TABLE 5

RESISTANCE TO ISOMERIZATION AFTER CYCLIZATION OF 5-(o-TOLYL)PENTENE-2 USING LOW ALUMINA ULTRASTABLE Y-TYPE CATALYST

| Batch | Temp, °C. | Reaction Time (Hr) | Wt. % OTP | Wt. % Useful In Product | Wt. % DMT Isom |
|---|---|---|---|---|---|
| 1 | Feed | 0 | 74 | 24.6 | 0.2 |
|  | 190 | 2 | 0 | 94.8 | 0.8 |
|  | 190 | 18 | 0 | 94.2 | 0.7 |

EXAMPLE 19-24

Additional Batch Runs Made with Used Low Alumina Ultrastable Y-Type Catalyst

Batch runs were made in a manner similar to that employed in Examples 9-16 employing a previously used Catalyst B from such Examples. Results are shown in Table 6, below. Temperature variations were made to observe the range of operability of the catalyst.

Batch run No. 8 was made under the same conditions as Batches Nos. 1 through 7 and demonstrates that the cracking of heavy by-products (Example 17, Table 4) was not detrimental to catalyst activity. Batch 9 indicates that an increase in temperature to 190° C. is not determined to catalyst performance. In Batch 10, the operation at 160° C. resulted in significantly lower reaction rates yielding incomplete conversion. The presence of a small amount of water in the distillate of Batch 10 indicated some catalyst poisoning. In Batch 11, the temperature of the catalyst was increased to accelerate the reaction and to drive off water from the previous batch. In Batch 12, the catalyst activity was noted to be lower than fresh catalyst, but still relatively high, yielding high conversion in 5.5 hours at 180° C. Finally, Batch 13 was conducted at a high temperature and demonstrates that even at such conditions selectivity and high yields could be obtained. For the entire series of 13 batch runs, the total OTP converted by the catalyst was 812 grams per gram of catalyst.

In all of these batch runs, the catalyst was Catalyst B from the first batch. The amount of catalyst was 7.2 grams. At the end of each batch run, the liquid in the reactor was subjected to flash distillation to leave a residue that was employed as the heel for the next succeeding batch. The residue remaining in the reactor at the end of 13 batch runs was 70.6 g. For all 13 batches, 5928 g of feedstock OTP were used and 5848 g of useful product was recovered by flash distillation. Total catalyst productivity was determined by the fact that 5848 g of OTP were converted with 7.2 g of Catalyst B so that 812 g of useful product per gram of catalyst was obtained.

TABLE 6
BATCH CYCLIZATION OF 5-(o-TOLYL)PENTENE-2 USING A USED LOW ALUMINA ULTRASTABLE Y-TYPE CATALYST TO DEMONSTRATE CATALYST STABILITY

| Example | Batch | Temp. C | Reaction Time (Hr) | Feedstock G Residue | G OTP | Dist. Prod Grams | Wt. % OTP In Prod. | Wt. % Useful In Prod. | Wt. % DMT Isom |
|---|---|---|---|---|---|---|---|---|---|
| 19 | 8 | 180 | 2.5 | 71.6 | 450.0 | 445.0 | 0.0 | 95.3 | 1.0 |
| 20 | 9 | 190 | 2.5 | 82.5 | 449.9 | 439.0 | 0.0 | 95.2 | 1.0 |
| 21 | 10 | 160 | 12.3 | 84.3 | 433.7 | 431.9 | 18.5 | 71.7 | 0.7 |
| 22 | 11 | 170–246 | 9.0 | 83.4 | 449.9 | 450.2 | 0.1 | 92.3 | 1.1 |
| 23 | 12 | 180 | 5.5 | 83.2 | 446.3 | 446.4 | 0.5 | 92.0 | 1.1 |
| 24 | 13 | 246 | 2.5 | 70.6 | 449.9 | 462.5 | 0.0 | 92.1 | 1.2 |

EXAMPLE 25

Continuous Cyclization of 5-(o-Tolyl)Pentene (OTP)

OTP was continuously fed to a stirred tank reactor equipped with an overhead condenser and maintained at reflux temperature for the reactor contents. The reflux temperature was modulated by adjusting the system pressure.

The product (DMT) was constantly removed from the overhead as a distillate. The heavy byproducts were retained in the reactor where they ultimately reached an equilibrium concentration, preventing further heavy formation.

The data presented in Table 7, below, illustrate 6 days of operation. The initial catalyst charge was a "low activity" sample of the Conteka 760 catalyst which required a reaction temperature of about 210° C. in the batch mode. After making 5 batch runs with this low activity catalyst, the hydrocarbon product from the 5th batch runs was used as the reaction medium for the continuous cyclization. On the first day of operation (first column), the distillate contained 94% useful components (2,6-Triad DMT+DMN, without the xylene impurity present in the feed) and only 1% of the sum of OTP and an intermediate convertable to product. During the first day of operation, the heavies in the reactor increased such that the overall yield for the first day (noted at the bottom of the table) was only 81.5% of the 2,6-triad. On Days 2–6 the distillate quality was similar to the first day. However, the heavy formation in the reactor decreased, and on Day 3, addition of fresh catalyst actually yielded a net loss of heavies in the system (negative yield).

The overall results for the continuous run after 6 days (55 hours) are presented in the far right column of Table 7. The average distillate contained 93.3% useful components (xylene-free basis) and the overall yield of the 2,6-triad DMT+DMNs was 92.5%.

TABLE 7
CONTINUOUS CYCLIZATION IN A STIRRED TANK REACTOR

| | Day 1 | 2 | 3 | 4 | 5 | 6 | For Overall Run |
|---|---|---|---|---|---|---|---|
| Feed G/Hr (Approx.) | 4 | 4 | 4 | 4 | 4 | 4 | |
| Type Catalyst | Used for 5 Batches | Add 3.5 G Fresh | | | | | |
| (Conteka CBV 760) | Low Activity | High Activity | | | | | |
| G Low Activity Cat. | 7.1 | 7.1 | 7.1 | 7.1 | 7.1 | 7.1 | 7.1 |
| G High Activity Cat. | 0 | 0 | 3.5 | 3.5 | 3.5 | 3.5 | 3.5 |
| wt. % Cat. in Reactor (Total) | 1.2 | 1.2 | 2 | 2 | 2 | 2 | 2 |
| Ave. Temp., °C. | 218 | 238 | 225 | 225 | 240** | 230–240 | 218–240 |
| Ave. Press, psia | 6.4 | 6.2 | 6.4 | 6.4 | 9–12 | 7–11 | 6–12 |
| Hrs. on Feed for Day | 6.7 | 13 | 10.1 | 8.1 | 10 | 7.1 | 55 |
| G of Feed into Reactor | 1259 | 2902 | 2235 | 1981 | 1670 | 1861 | 11916 |
| Cumulative-End of Day | | | | | | | |
| Hrs. on Low Act. Cat. | 37 | 50 | 60 | 68 | 78 | 85 | 85 |
| Hrs. On Hi Act. Cat. | — | — | 10 | 18 | 28 | 35 | 35 |
| G Feed into Reactor | 3644 | 6546 | 8781 | 10762 | 12432 | 14301 | 14301 |
| G Feed/G Cat. | 513 | 922 | 828 | 1015 | 1173 | 1349 | 1349 |
| Average Product (Distillate) Composition for Each Day—Weight Percent | | | | | | | |
| o-Xylene | 1.5 | 1.1 | 1.1 | 1.1 | 0.8 | 0.9 | 1.1 |
| SAT OTP | 1.7 | 1.5 | 2.4 | 2.2 | 2.9 | 2.1 | 2.1 |
| OTP + Intermed. | 1.0 | 3.2 | 0.9 | 1.1 | 0.5 | 0.8 | 1.4 |
| 2,6-Triad DMT + DMN* | 92.6 | 90.7 | 92.9 | 93.0 | 91.7 | 93.4 | 92.3 |
| 2,7-Triad DMT | 0.9 | 0.9 | 0.8 | 0.8 | 0.9 | 0.9 | 0.9 |
| Heavy | 0.0 | 0.0 | 0.1 | 0.2 | 0.6 | 0.0 | 0.1 |
| Other | 2.3 | 2.5 | 1.8 | 1.5 | 2.6 | 1.8 | 2.1 |
| TOTAL | 100.0 | 100.0 | 100.0 | 100.0 | 100.0 | 100.0 | 100.0 |
| *2,6-Triad w/o Xylene | 94.0 | 91.7 | 93.9 | 94.0 | 92.5 | 94.3 | 93.3 |
| Average Daily Yields—Including Change in Reactor Composition and Quality G Component/100 G Tolylpentenes | | | | | | | |
| Sat. OTP | 1.5 | 1.5 | 2.7 | 2.2 | 3.0 | 2.0 | 2.1 |
| OTP | 0.9 | 3.2 | 1.0 | 1.1 | 0.5 | 0.8 | 1.4 |
| 2,6-Triad DMT + DMN | 81.5 | 89.1 | 102.7 | 93.2 | 96.0 | 88.5 | 92.5 |
| 2,7-Triad DMT | 0.8 | 0.9 | 0.9 | 0.8 | 0.9 | 0.9 | 0.9 |
| Heavy | 13.3 | 2.8 | −9.3 | 1.1 | −3.2 | 6.2 | 1.0 |
| Other | 2.0 | 2.5 | 1.9 | 1.5 | 2.7 | 1.7 | 2.1 |
| TOTAL | 100.0 | 100.0 | 100.0 | 100.0 | 100.0 | 100.0 | 100.0 |

Although the present invention has been described and illustrated based on the presently available information and embodiments, it is to be understood that modifications and variations are within the spirit and scope of the invention, as those skilled in the art will readily appreciate and that such are within the purview and scope of the appended claims.

We claim:

1. A method for cyclizing an alkenylbenzene having the formula

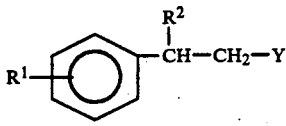

wherein $R^1$ is a member of the group consisting of hydrogen, methyl and ethyl, $R^2$ is a member of the group consisting of hydrogen and methyl, and Y is an alkenyl of the group consisting of —CH=CH—CH$_3$ and —CH$_2$—CH=CH$_2$ which comprises contacting said alkenylbenzene in liquid form and having a water content of no more than about 0.1 weight percent with a solid cyclization catalyst constituted by a relatively low acidity, ultrastable, hydrogen form of crystalline aluminosilicate zeolite Y having an average of no more than about 10 framework Bronsted acid sites per unit cell, a unit cell size no greater than about 24.3 Angstroms, a silica-to-alumina bulk molar ratio of at least about 12, and a sodium content of no more than about 0.4 percent by weight, calculated as elemental sodium and based on the weight of the zeolite; or in terms of the sodium oxide-to-alumina bulk molar ratio in the range of about 0.001:1 to less than about 1:1, at a temperature in the range of about 120° C. to about 350° C.; and for a time period sufficient to produce a liquid product enriched in a dialkyltetrahydronaphthalene.

2. The method of claim 1 wherein said temperature is in the range of about 160° C. to about 250° C.

3. The method of claim 1 wherein said alkenylbenzene is combined with preformed dialkyltetrahydronaphthalene.

4. The method of claim 1 practiced continuously.

5. The method of claim 1 practiced batchwise.

6. The method of claim 5 wherein said zeolite catalyst is a powder, and said contacting occurs in a stirred tank reactor.

7. The method of claim 1 wherein said alkenylbenzene is 5-(monomethylphenyl)pent-1-ene.

8. The method of claim 1 wherein said alkenylbenzene is 5-(monomethylphenyl)pent-2-ene.

9. The method of claim 1 wherein said alkenylbenzene is 5-(phenyl)-hex-1-ene.

10. The method of claim 1 wherein said alkenylbenzene is 5-(phenyl)-hex-2-ene.

11. The method of claim 1 wherein said alkenylbenzene is 5-(o-tolyl)-pent-2-ene.

12. The method of claim 1 wherein said alkenylbenzene is 5-(o-tolyl)-pent-1-ene.

13. The method of claim 1 wherein said zeolite catalyst is supported on a porous refractory inorganic oxide.

14. The method of claim 13 wherein the zeolite catalyst constitutes about 10 to about 90 percent by weight of the total weight of supported catalyst.

15. The method of claim 13 wherein the zeolite catalyst constitutes about 20 to about 80 percent by weight of the total weight of supported catalyst.

16. A method for cyclizing an alkenylbenzene having the formula

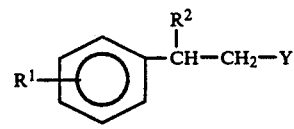

wherein
$R^1$ is a member of the group consisting of hydrogen, methyl, and ethyl,
$R^2$ is a member of the group consisting of hydrogen and methyl, and Y is an alkenyl of the group consisting of CH=CH—CH$_3$ and —CH$_2$—CH=CH$_2$
which comprises the steps of:
(a) initially forming in a stirred tank reactor an initiator batch comprising a non-reactive hydrocarbon which is in a liquid phase at a temperature in the range of about 160° to about 250° C. and at a pressure in the range of about 2.5 to about 525 pounds per square inch absolute, and a powdered cyclization catalyst constituted by a relatively low acidity, ultrastable hydrogen form of crystalline aluminosilicate zeolite Y having an average of no more than about 10 framework Bronsted acid sites per unit cell, a unit cell size no greater than about 24.3 Angstorms, a silica-to-alumina bulk molar ratio of at least about 12, and a sodium content of no more than about 0.4 percent by weight, calculated as elemental sodium and based on the weight of said zeolite, or in terms of the sodium oxide-to-alumina bulk molar ratio in the range of about 0.001:1 to less than about 1 and
(b) adding to said initiator batch in said stirred tank reactor under liquid phase conditions an aliquot of an alkenylbenzene having the formula,

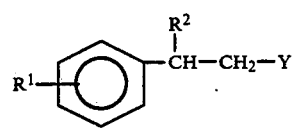

wherein
$R^1$ is a member of the group consisting of hydrogen, methyl, and ethyl,
$R^2$ is a member of the group consisting of hydrogen and methyl, and
Y is an alkenyl of the group consisting of —CH=CH—CH$_3$ and —CH$_2$—CH=CH$_2$,
said alkenylbenzene being substantially free of non-hydrocarbon components, and contacting said alkenylbenzene with said zeolite catalyst under liquid phase conditions at a temperature in the range of about 120° C. to about 350° C. for a time period sufficient to produce a liquid product enriched in dialkyltetrahydronaphthalene.

17. The process of claim 16 wherein said non-reactive hydrocarbon comprises a dialkyltetrahydronaphthalene.

18. The method of claim 16 wherein said adding is carried out at a rate which maintains the reaction temperature within said temperature range.

19. The method of claim 16 wherein the concentration of said zeolite catalyst is in the range of about 0.1 to about 10 weight percent based on total reactor charge.

20. The method of claim 16 wherein said catalyst concentration is in the range of about 0.3 to about 2 weight percent.

21. The method of claim 16 wherein produced dialkyltetrahydronaphthalene is removed from said tank reactor by flash distillation while leaving in said tank reactor a heel composition comprising said zeolite catalyst, residual dialkyltetrahydronaphthalenes, and hydrocarbon by-products having molecular weights higher than that of said residual dialkyltetrahydronaphthalenes.

22. The method of claim 21 wherein thereafter another aliquot of said alkenylbenzene is added to said heel composition, said alkenylbenzene in liquid form is contacted at a temperature in the range of about 120° C. to about 350° C. with said zeolite catalyst for a time period sufficient to produce a liquid product enriched in said dialkyltetrahydronaphthalene, after which said flash distillation is repeated.

23. The method of claim 22 repeated at least once.

24. The method of claim 21 wherein said heel composition in said tank reactor is heated to a temperature in the range of about 180° C. to about 350° C. at a pressure sufficient to maintain said heel composition substantially in a liquid phase, thereby cracking said composition and forming dimethyltetrahydronaphthalene which is concurrently removed by flash distillation from said tank reaction zone.

25. A batch method for making 1,5-dimethyltetrahydronaphthalene by cyclizing 5-(o-tolyl)-pent-2-ene comprising the steps of
    (a) contacting an aliquot of substantially pure 5-(o-tolyl)-pent-2-ene with a catalytically effective amount of a solid cyclization catalyst constituted by a substantially neutral, ultrastable, hydrogen form of crystalline aluminosilicate zeolite Y having an average of no more than about 10 framework Bronsted acid sites per unit cell, a unit cell size no greater than about 24.3 Angstroms, a silica-to-alumina bulk molar ratio of at least about 12, and a sodium content of no more than about 0.4 percent by weight calculated as elemental sodium and based on the weight of said zeolite Y or in terms of the sodium oxide-to-alumina bulk molar ratio in the range of about 0.001:1 to less than about 1:1, at a temperature in the range of about 120° C. to about 350° C. under liquid phase conditions for a time period sufficient to substantially convert said 5-(o-tolyl)-pent-2-ene into a liquid composition enriched in 1,5-dimethyltetrahydronaphthalene;
    (b) adding to said liquid product another aliquot of substantially pure 5-(o-tolyl)-pent-2-ene while maintaining said temperature and said liquid phase conditions, said adding being carrier out at a rate which allows heat removal and control of said temperature at a reflux level within said temperature range;
    (c) maintaining said reflux temperature level while reducing said pressure at a rate sufficient to maintain said reflux level until said 5-(o-tolyl)-pent-2-ene is substantially converted into a liquid product enriched in 1,5-dimethyltetrahydronaphthalene; and
    (d) flash distilling from said liquid product at least about 70 weight percent of said 1,5-dimethyltetrahydronaphthalene therein and leaving a residual liquid composition.

26. The method of claim 25 wherein the step sequence of said steps (b), (c) and (d) is repeated at least once.

27. The method of claim 26 wherein said step sequence is repeated at least 6 times.

28. The method of claim 25 wherein, after step (d), said residual composition in said reaction zone is further processed by heating said composition to a temperature in the range of about 180° C. to about 350° C. while maintaining a pressure sufficient to maintain said composition substantially in a liquid phase and concurrently flash distilling from said reaction zone 1,5-dimethyltetrahydronaphthalene.

* * * * *

UNITED STATES PATENT AND TRADEMARK OFFICE
CERTIFICATE OF CORRECTION

PATENT NO. : 5,034,561
DATED : July 23, 1991
INVENTOR(S) : Sikkenga, et. al.

It is certified that error appears in the above-indentified patent and that said Letters Patent is hereby corrected as shown below:

| Column | Line | |
|---|---|---|
| 4 | 3 | "Valley Forge, Penna.," should read --Valley Forge, Penn.,-- |
| 8 | 35-40 | 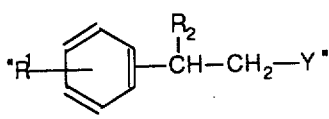 should be deleted and replaced with: |

--TABLE 1

CATALYST CHARACTERISTICS

| Catalyst | Cell Size (Angstroms) | $SiO_2/Al_2O_3$ Bulk Molar Ratio | $Na_2O$ Content (Wt.%) | $Na_2O/Al_2O_3$ Bulk Molar Ratio |
|---|---|---|---|---|
| Catalyst A | 24.51 | 5.1 | 2.5 | 0.17 |
| Catalyst B | 24.20 | 42 | 0.05 | 0.05-- |

UNITED STATES PATENT AND TRADEMARK OFFICE
CERTIFICATE OF CORRECTION

PATENT NO. : 5,034,561
DATED : July 23, 1991
INVENTOR(S) : Sikkenga, et. al.

It is certified that error appears in the above-indentified patent and that said Letters Patent is hereby corrected as shown below:

| Column | Line |
|---|---|
| 9-10 | Table 3 |

"Wt.% Useful In Product   Wt.% DMT Isom

TOTALS         95.7            0.90"

should read:

--Wt.% Useful In Product   Wt.% DMT Isom

TOTALS         ____            ____

Average        95.7            0.90--

| Column | Line | |
|---|---|---|
| 10 | 2 | "OTP (84%)." should read --OTP (85%).-- |
| 11 | 8-9 | "with a selectivety of 88 wt %." should read --with a selectivity of 88 wt %.-- |
| 11 | 41 | "a batch conversion" should read --A batch conversion-- |

UNITED STATES PATENT AND TRADEMARK OFFICE
CERTIFICATE OF CORRECTION

Page 3 of 3

PATENT NO. : 5,034,561
DATED : July 23, 1991
INVENTOR(S) : Sikkenga, et. al.

It is certified that error appears in the above-indentified patent and that said Letters Patent is hereby corrected as shown below:

<u>Column</u>   <u>Line</u>

14   Table 7   "

| Day | | |
|---|---|---|
| 2 | 3 | 4 |
| 4 | 4 | 4 |
| | Add 3.5 G Fresh" | | should read:

--

| Day | | |
|---|---|---|
| 2 | 3 | 4 |
| 4 | 4 | 4 |
| | Add 3.5 G Fresh High Activity-- | |

16   15   "of 13 CH=CH-CH$_3$" should read -- CH=CH-CH$_3$- --

Signed and Sealed this

Twenty-eighth Day of September, 1993

Attest:

BRUCE LEHMAN

Attesting Officer    Commissioner of Patents and Trademarks